(12) United States Patent
Breece et al.

(10) Patent No.: US 6,870,034 B2
(45) Date of Patent: Mar. 22, 2005

(54) PROTEIN PURIFICATION

(75) Inventors: Timothy N. Breece, San Francisco, CA (US); Robert L. Fahrner, San Mateo, CA (US); Jeffrey R. Gorrell, San Bruno, CA (US); Kathlyn Pham Lazzareschi, San Mateo, CA (US); Philip M. Lester, San Lorenzo, CA (US); David Peng, Daly City, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 10/356,974

(22) Filed: Feb. 3, 2003

(65) Prior Publication Data

US 2003/0153735 A1 Aug. 14, 2003

Related U.S. Application Data

(60) Provisional application No. 60/354,579, filed on Feb. 5, 2002.

(51) Int. Cl.$^7$ .................................................. C07K 1/22
(52) U.S. Cl. ........................ 530/413; 436/824; 436/828
(58) Field of Search ......................... 530/413; 436/824, 436/828

(56) References Cited

U.S. PATENT DOCUMENTS

| | | | | |
|---|---|---|---|---|
| 5,429,746 A | * | 7/1995 | Shadle et al. ............... | 210/635 |
| 5,683,916 A | * | 11/1997 | Goffe et al. ................. | 436/535 |
| 5,726,293 A | * | 3/1998 | Seed ........................... | 530/413 |
| 5,981,299 A | * | 11/1999 | Lance, III et al. .......... | 436/547 |
| 5,994,511 A | | 11/1999 | Lowman et al. ......... | 530/387.3 |
| 6,037,454 A | | 3/2000 | Jardieu et al. ............ | 530/387.3 |
| 6,127,526 A | * | 10/2000 | Blank .......................... | 530/413 |
| 6,333,398 B1 | | 12/2001 | Blank .......................... | 530/413 |

OTHER PUBLICATIONS

Roberts et al, Basic Principles of Organic Chemistry, W. A. Benjamin, Inc., 1964, pp. 378–379, 1964.*
Scamehore et al (EDS.), Surfactant—Based Separation: Science and Technology, American Chemical Society, 2000, p. 27.*
Chadha and Sulkowski, "Chromatography of Human Leukocyte Interferon on Controlled Pore Glass." *Preparative Biochemistry* 11(4):467–482 (1981).
Reifsnyder et al., "Purification of Insulin–Like Growth Factor–I and Related Proteins Using Underivatized Silica." *J. Chromatography A*. 753:73–80 (1996).
Sulkowski, Eugene, "Controlled Pore Glass Chromatography of Proteins" *Protein Purification: Micro to Macro* (Proceedings of Cetus–UCLA Symposium—Frisco, Colorado), Richard Burgess, New York:A.R. Liss vol. 68:177–195 (Mar. 20–Apr. 4, 1987).
S. Hjertén, J. Rosengen, and S. Pâhlman, Biochim. Biophys. Acta, 101, 281–288 (1974).
S. Hjertén, J. Chromatogr., 12, 510–526 (1963).
S. Hjertén, S. Höglund, and G. Ruttkay–Nedecky, Acta Virol., 14, 89–101 (1970).
L. Wide, R. Axén, and J. Porath, Immunochemistry, 4, 381–386 (1967).
L. Wide, S.J. Nillius, C.A. Gemzell, and P. Roos, Acta Endocrinol., Suppl. 174, 1–58 (1973).
C.S. Nicoll, Endocrinology, 80, 641–655 (1967).
P.E. Hexner, L.E. Radford, and J.W. Beams, Proc. Natl. Acad. Sci. U.S., 47, 1848–1852 (1961).
C.H. Chervenka, Anal. Biochem., 34, 24–29 (1970).
D.H. Spackman, W.H. Stein, and S. Moore, Anal. Chem., 30, 1190–1206 (1958).
S. Moore, J. Biol. Chem., 238, 235–237 (1963).
I.M. Klotz, D.W. Darnall, and N.R. Langerman, in "The Proteins", H. Neurath and R.L. Hill, eds., Academic Press, New York, 1975, pp. 293–411.
A.J. Cornish–Bowden and O.E. Koshland, Jr., J. Biol. Chem., 246, 3092–3102 (1971).
F. Nyberg, P. Roos, and L. Wide, Biochim. Biophys. Acta, 625, 255–265 (1980).
B.H.J. Hofstee, Anal. Biochem., 52, 430–447 (1973).
A.B. Robinson, J.H. McKerrow, and P. Cary, Proc. Natl. Acad. Sci. U.S., 66, 753–757 (1970).
R. Shenai and M. Wallis, Biochem. J., 182, 735–743 (1979).

\* cited by examiner

*Primary Examiner*—David Saunders
(74) *Attorney, Agent, or Firm*—Wendy Lee; Ginger R. Dreger; Heller Ehrman White & McAuliffe, LLP

(57) ABSTRACT

A method for purifying proteins by Protein A chromatography is described which comprises removing contaminants by washing the solid phase with various intermediate wash buffers.

19 Claims, 9 Drawing Sheets

LIGHT CHAIN

```
1                              15                          30                               45
D I Q M T Q S P S S L S A S V G D R V T I T C R A S Q D V N T A V A W Y Q Q K P G K A P K
46                             60                          75                               90
L L I Y S A S F L Y S G V P S R F S G S R S G T D F T L T I S S L Q P E D F A T Y Y C Q Q
91                             105                         120                              135
H Y T T P P T F G Q G T K V E I K R T V A A P S V F I F P P S D E Q L K S G T A S V V C L
136                            150                         165                              180
L N N F Y P R E A K V Q W K V D N A L Q S G N S Q E S V T E Q D S K D S T Y S L S S T L T
181                            195                    210  214
L S K A D Y E K H K V Y A C E V T H Q G L S S P V T K S F N R G E C         SEQ ID NO: 1
```

FIG._1A

HEAVY CHAIN

```
1   EVQLVESGGGLVQPGGSLRLSCAASGFNIKDTYIHWVRQAPGKGL
46  EWVARIYPTNGYTRYADSVKGRFTISADTSKNTAYLQMNSLRAED
91  TAVYYCSRWGGDGFYAMDYWGQGTLVTVSSASTKGPSVFPLAPSS
136 KSTSGGTAALGCLVKDYFPEPVTVSWNSGALTSGVHTFPAVLQSS
181 GLYSLSSVVTVPSSSLGTQTYICNVNHKPSNTKVDKKVEPKSCDK
226 THTCPPCPAPELLGGPSVFLFPPKPKDTLMISRTPEVTCVVVDVS
271 HEDPEVKFNWYVDGVEVHNAKTKPREEQYNSTYRVVSVLTVLHQD
316 WLNGKEYKCKVSNKALPAPIEKTISKAKGQPREPQVYTLPPSREE
361 MTKNQVSLTCLVKGFYPSDIAVEWESNGQPENNYKTTPPVLDSDG
406 SFFLYSKLTVDKSRWQQGNVFSCSVMHEALHNHYTQKSLSLSPG  449
```

SEQ ID NO: 2

FIG._1B

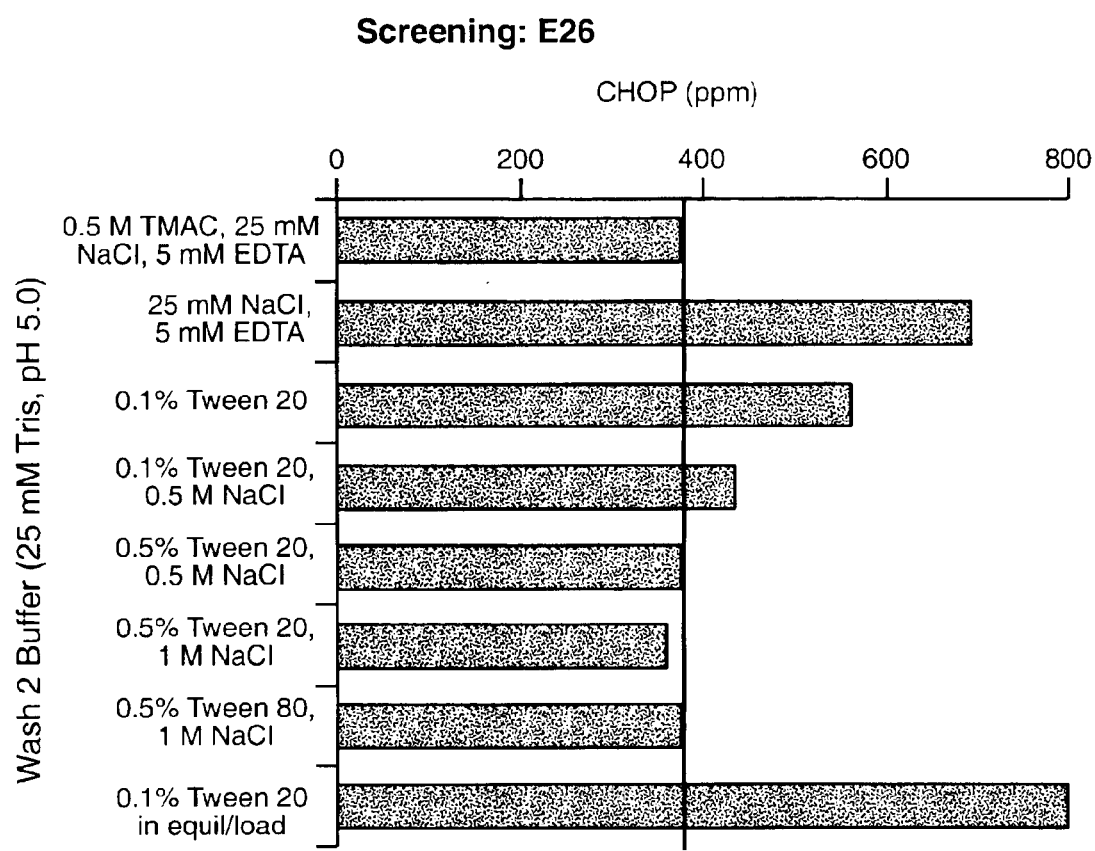
FIG._2

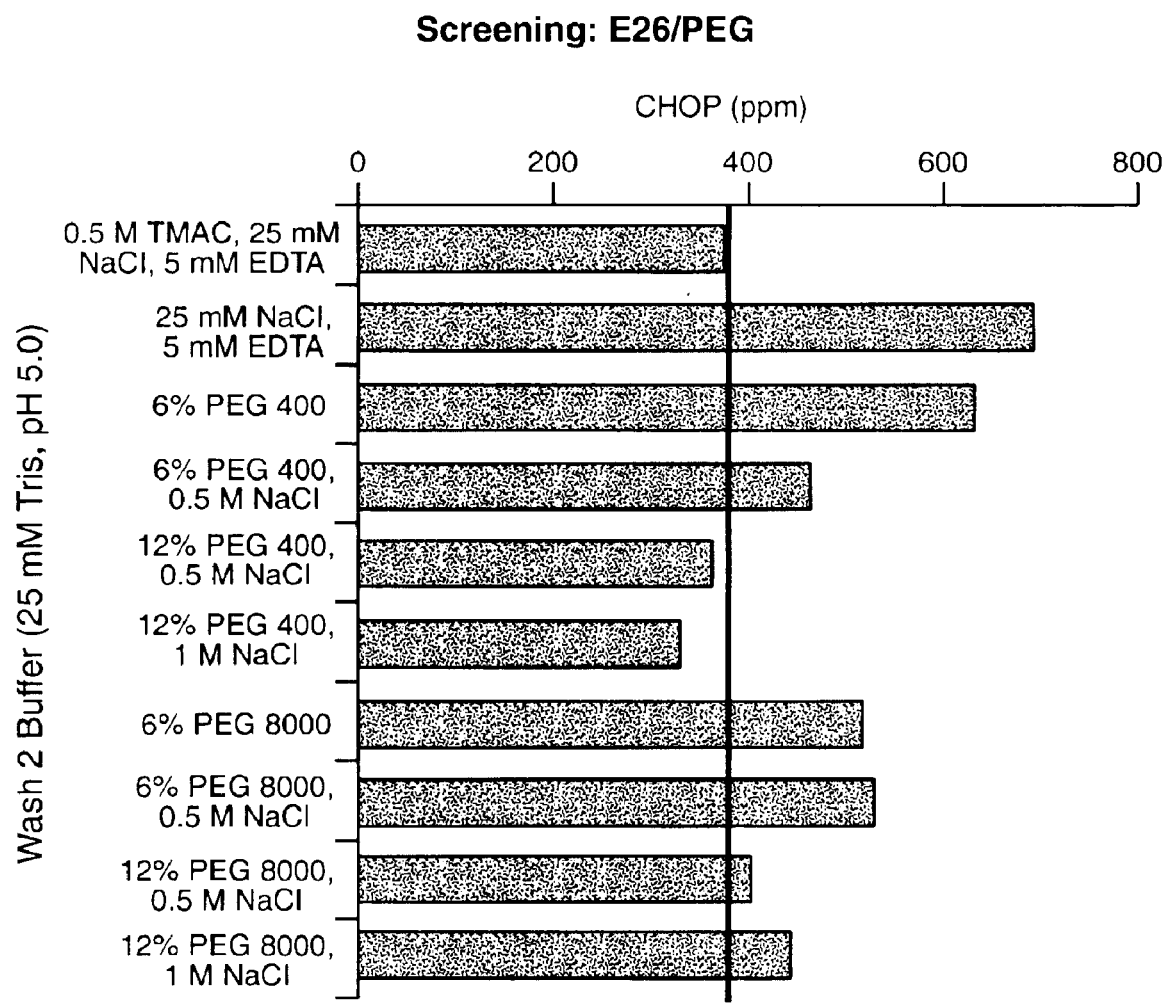
FIG._3

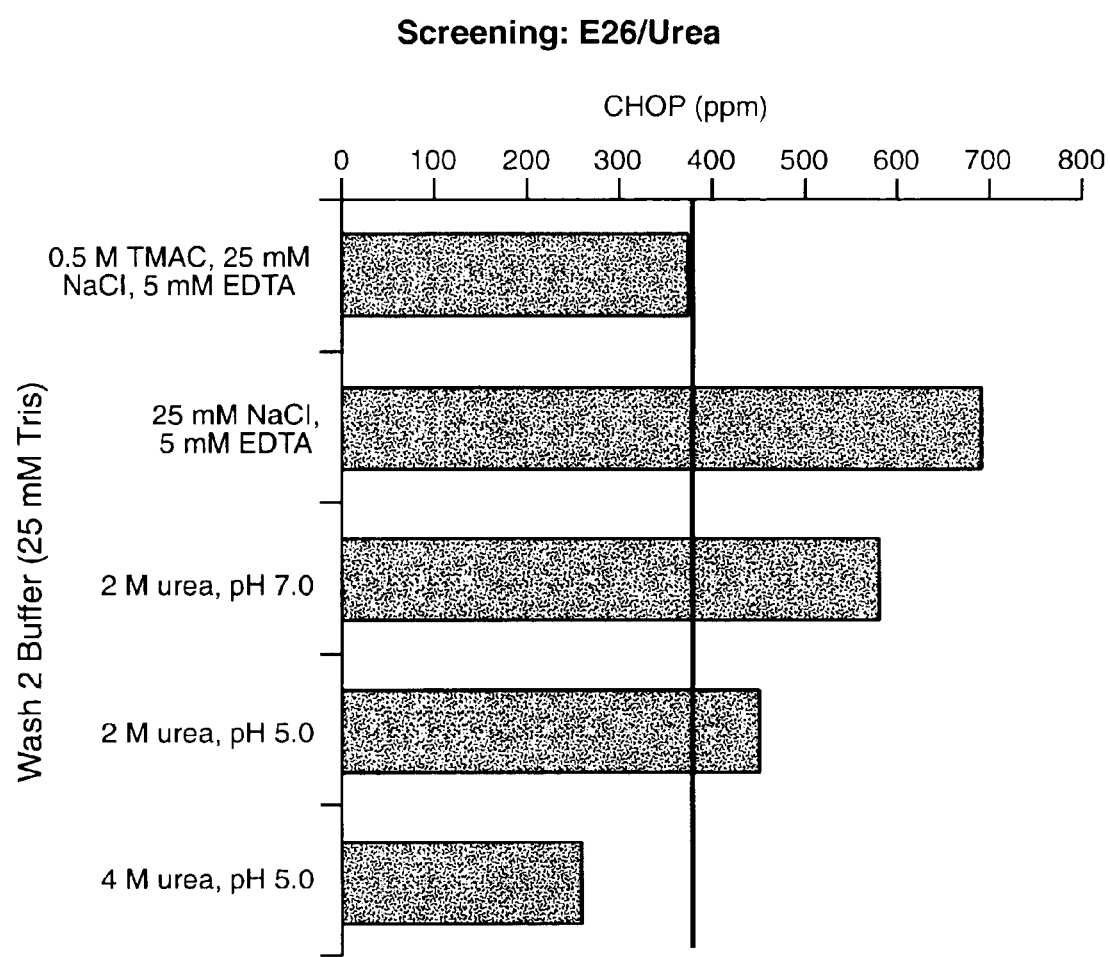
FIG._4

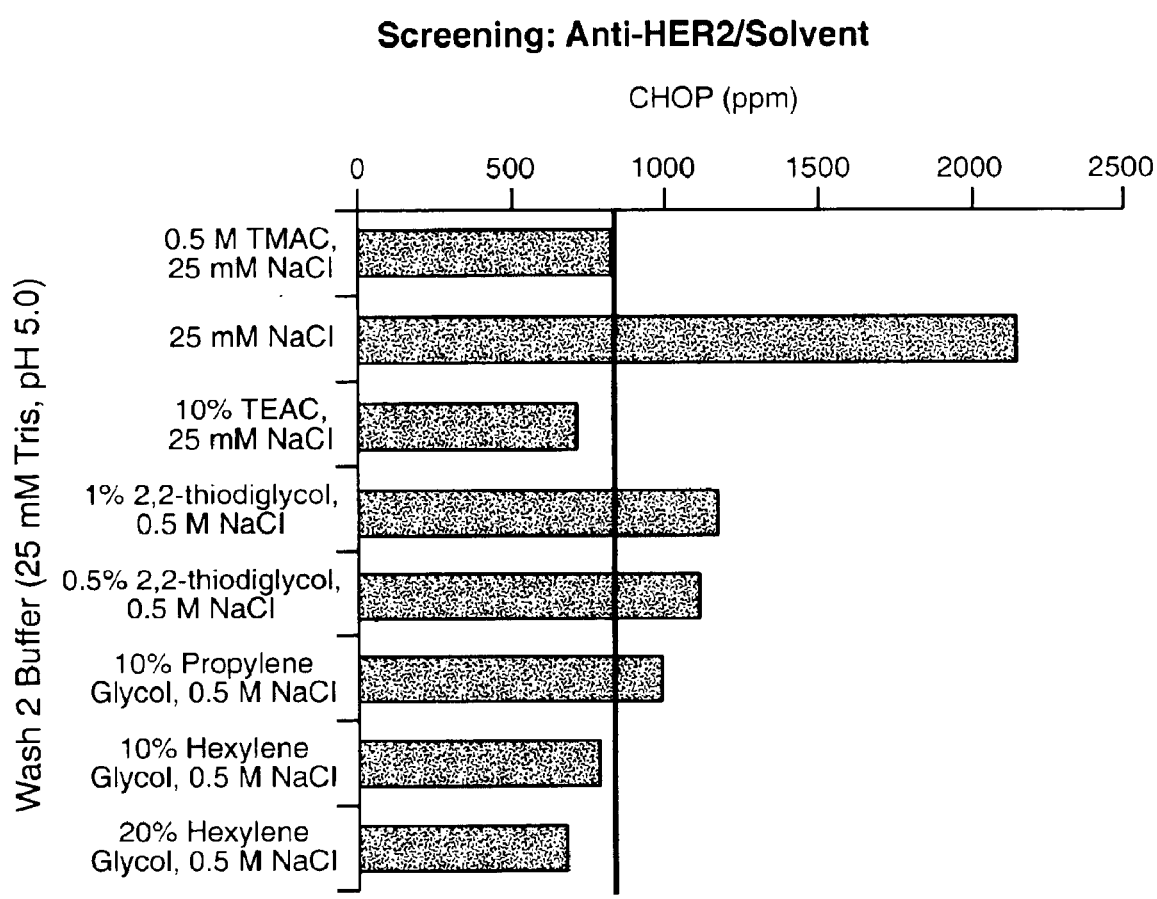
FIG._5

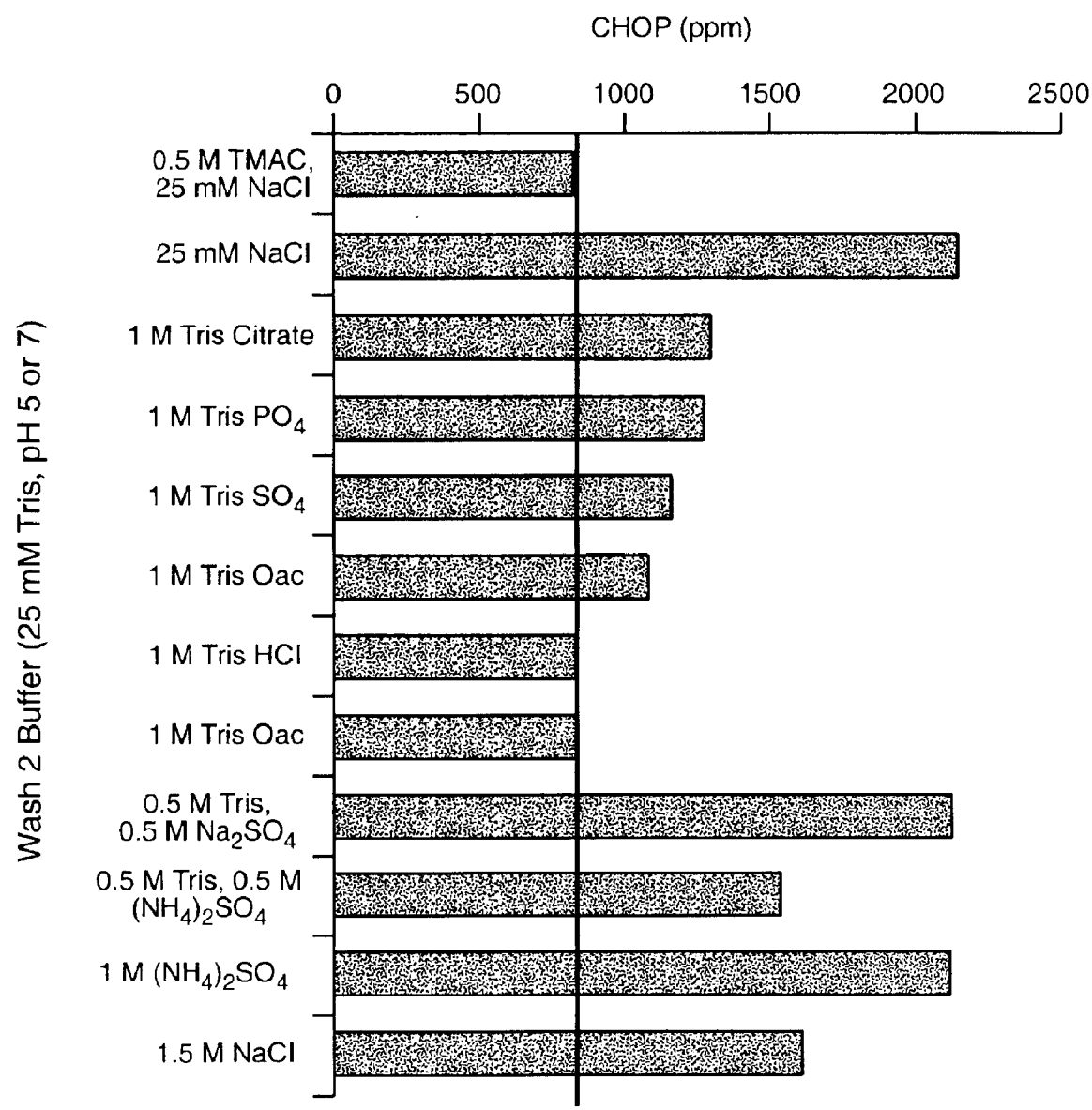
FIG._6

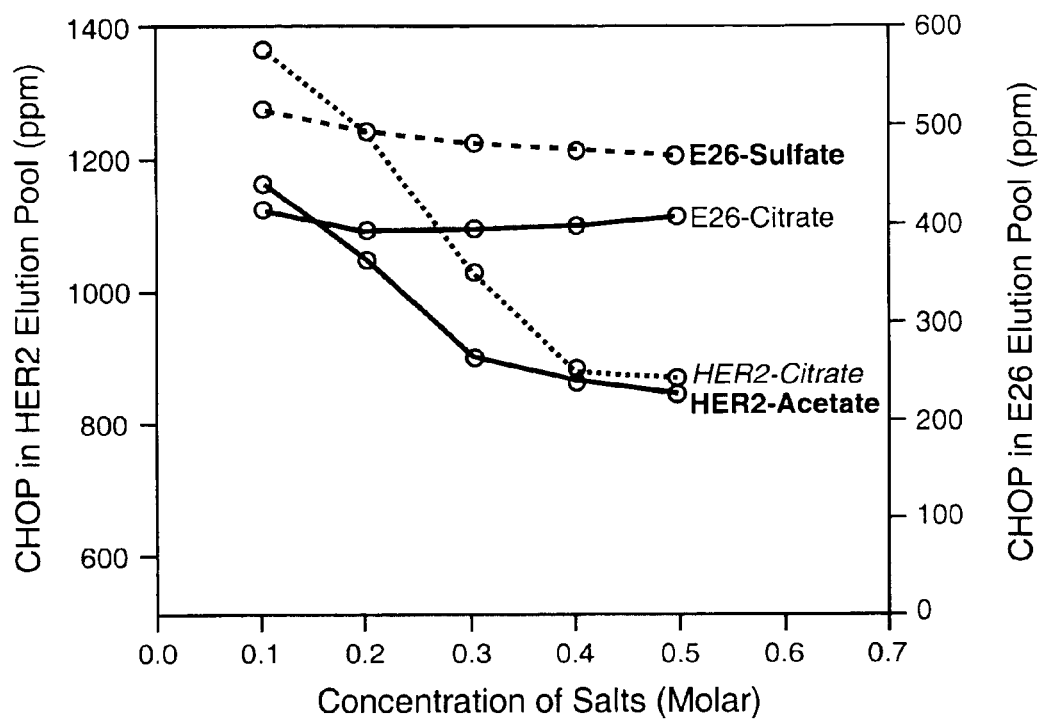
FIG._7
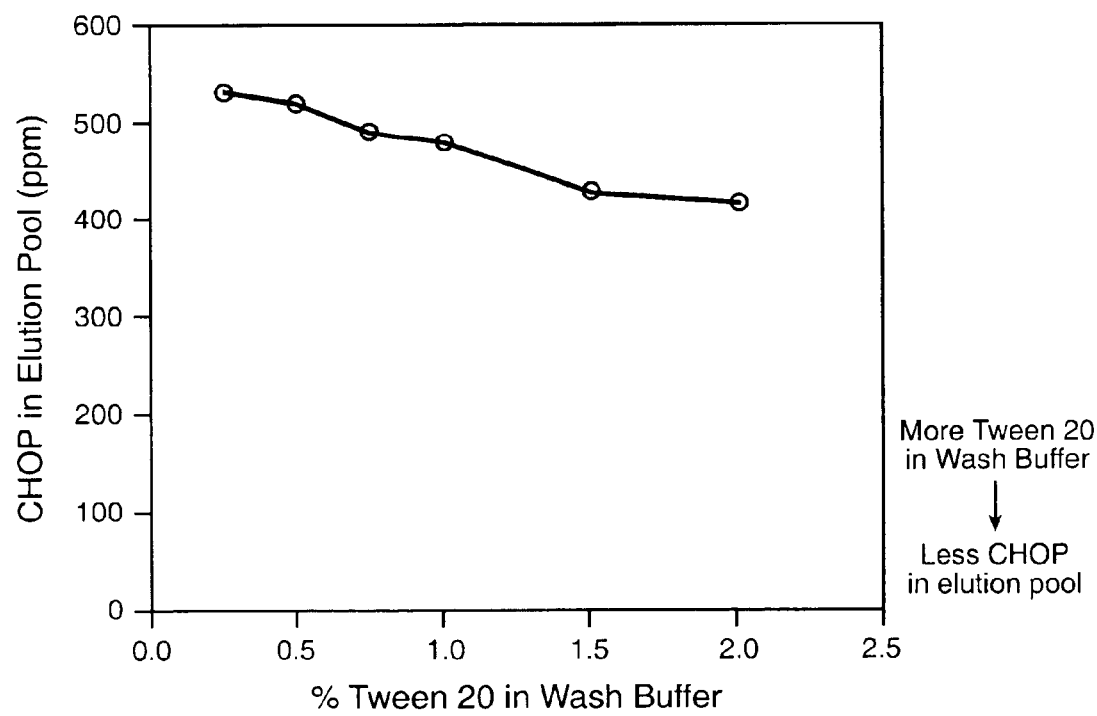
FIG._8

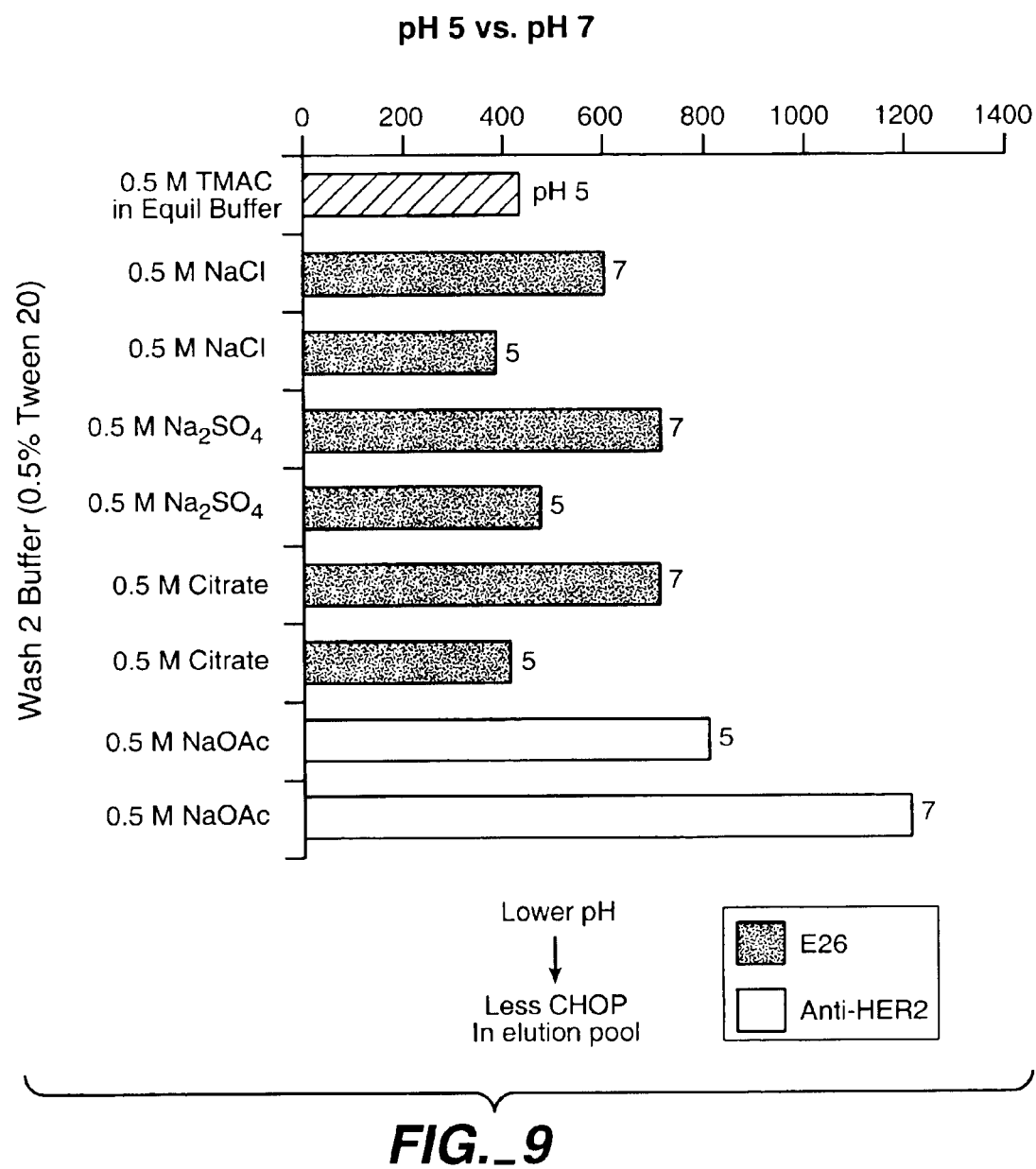
FIG._9

PROTEIN PURIFICATION

This is a non-provisional application claiming priority under 35 USC §119 to provisional application No. 60/354,579 filed Feb. 5, 2002, the entire disclosure of which is hereby incorporated by reference.

BACKGROUND OF THE INVENTION

1. Field of the Invention

This invention relates generally to protein purification. In particular, the invention relates to a method for purifying $C_H2/C_H3$ region-containing proteins, such as antibodies and immunoadhesins, by Protein A affinity chromatography.

2. Description of Related Art

The large-scale, economic purification of proteins is increasingly an important problem for the biotechnology industry. Generally, proteins are produced by cell culture, using either mammalian or bacterial cell lines engineered to produce the protein of interest by insertion of a recombinant plasmid containing the gene for that protein. Since the cell lines used are living organisms, they must be fed with a complex growth medium, containing sugars, amino acids, and growth factors, usually supplied from preparations of animal serum. Separation of the desired protein from the mixture of compounds fed to the cells and from the by-products of the cells themselves to a purity sufficient for use as a human therapeutic poses a formidable challenge.

Procedures for purification of proteins from cell debris initially depend on the site of expression of the protein. Some proteins can be caused to be secreted directly from the cell into the surrounding growth media; others are made intracellularly. For the latter proteins, the first step of a purification process involves lysis of the cell, which can be done by a variety of methods, including mechanical shear, osmotic shock, or enzymatic treatments. Such disruption releases the entire contents of the cell into the homogenate, and in addition produces subcellular fragments that are difficult to remove due to their small size. These are generally removed by differential centrifugation or by filtration. The same problem arises, although on a smaller scale, with directly secreted proteins due to the natural death of cells and release of intracellular host cell proteins in the course of the protein production run.

Once a clarified solution containing the protein of interest has been obtained, its separation from the other proteins produced by the cell is usually attempted using a combination of different chromatography techniques. These techniques separate mixtures of proteins on the basis of their charge, degree of hydrophobicity, or size. Several different chromatography resins are available for each of these techniques, allowing accurate tailoring of the purification scheme to the particular protein involved. The essence of each of these separation methods is that proteins can be caused either to move at different rates down a long column, achieving a physical separation that increases as they pass further down the column, or to adhere selectively to the separation medium, being then differentially eluted by different solvents. In some cases, the desired protein is separated from impurities when the impurities specifically adhere to the column, and the protein of interest does not, that is, the protein of interest is present in the "flow-through."

Affinity chromatography, which exploits a specific interaction between the protein to be purified and an immobilized capture agent, may also be an option for some proteins. Protein A is a useful adsorbent for affinity chromatography of proteins, such as antibodies, which contain an Fc region. Protein A is a 41 kD cell wall protein from *Staphylococcus aureus* which binds with a high affinity (about $10^{-8}$M to human IgG) to the Fc region of antibodies.

Proteins may be purified using controlled pore glass (Sulkowski, E. *Protein Purification: Micro to Macro*, pgs 177–195 (1987); Chadha et al. *Preparative Biochemistry* 11(4):467–482 (1981)) or underivatized silica (Reifsnyder et al. *J. Chromatography* 753:73–80 (1996)).

U.S. Pat. Nos. 6,127,526 and 6,333,398 (Blank, G.) describe an intermediate wash step during Protein A chromatography using hydrophobic electrolytes,e.g., tetramethylammonium chloride (TMAC) and tetraethylammonium chloride (TEAC), to remove the contaminants, but not the immobilized Protein A or the protein of interest, bound to the Protein A column.

SUMMARY OF THE INVENTION

The present invention provides various intermediate wash buffers, other than TMAC or TEAC, for use in Protein A chromatography.

In one embodiment, the invention provides a method for purifying a protein which comprises a $C_H2/C_H3$ region, from a contaminated solution thereof by Protein A chromatography comprising: (a) adsorbing the protein to Protein A immobilized on a solid phase; (b) removing contaminants by washing the solid phase with a composition comprising detergent and salt; and (c) recovering the protein from the solid phase.

In another embodiment, the invention provides a method for purifying a protein, which comprises a $C_H2/C_H3$ region, from a contaminated solution thereof by Protein A chromatography comprising: (a) adsorbing the protein to Protein A immobilized on a solid phase; (b) removing contaminants by washing the solid phase with a composition comprising a buffer at a concentration of greater than about 0.8M; and (c) recovering the protein from the solid phase.

The invention also pertains, in another embodiment, to a method for purifying a protein, which comprises a $C_H2/C_H3$ region, from a contaminated solution thereof by Protein A chromatography comprising: (a) adsorbing the protein to Protein A immobilized on a solid phase; (b) removing contaminants by washing the solid phase with a composition comprising salt and solvent; and (c) recovering the protein from the solid phase.

Moreover, the invention provides a method for purifying a protein, which comprises a $C_H2/C_H3$ region, from a contaminated solution thereof by Protein A chromatography comprising: (a) adsorbing the protein to Protein A immobilized on a solid phase; (b) removing contaminants by washing the solid phase with a composition comprising salt and polymer; and (c) recovering the protein from the solid phase.

In preferred embodiments, the protein is an antibody (e.g. one which binds HER2, vascular endothelial growth factor (VEGF), IgE, CD20, CD40, CD11a, tissue factor (TF), prostate stem cell antigen (PSCA), interleukin-8 (IL-8), epidermal growth factor receptor (EGFR), HER3, HER4α4β7 or α5β3) or an immunoadhesin (e.g. a TNF receptor immunoadhesin).

BRIEF DESCRIPTION OF THE DRAWINGS

FIGS. 1A–B show the light chain amino acid sequence (SEQ ID NO:1) and heavy chain amino acid sequence (SEQ ID NO:2) of Trastuzumab (HERCEPTIN®).

FIG. 2 depicts screening of various intermediate wash buffers with regard to the anti-IgE antibody E26. The amount of Chinese Hamster Ovary Protein (CHOP) contamination in the elution pool (ppm) is depicted.

FIG. 3 shows screening of intermediate wash buffers containing polyethylene glycol (PEG). The antibody is E26.

FIG. 4 illustrates screening of urea intermediate washes, where the antibody is E26.

FIG. 5 depicts screening of various intermediate wash buffers with regard to the anti-HER2 antibody Trastuzumab. The amount of CHOP in the elution pool (ppm) is depicted.

FIG. 6 depicts screening of various intermediate wash buffers with regard to Trastuzumab and a humanized anti-CD11a antibody.

FIG. 7 shows CHOP in the Protein A pool for Trastuzumab and an intermediate wash buffer including sodium citrate or sodium acetate salt; or E26 and an intermediate wash buffer including sodium sulfate or sodium citrate salt.

FIG. 8 represents alteration of polysorbate 20 in the intermediate wash buffer for E26.

FIG. 9 illustrates the effect of pH on CHOP in the elution pool for Trastuzumab and E26.

DETAILED DESCRIPTION OF THE PREFERRED EMBODIMENTS

Definitions:

When used herein, the term "Protein A" encompasses Protein A recovered from a native source thereof, Protein A produced synthetically (e.g. by peptide synthesis or by recombinant techniques), and variants thereof which retain the ability to bind proteins which have a $C_H2/C_H3$ region. Protein A can be purchased commercially from Repligen, Pharmacia and Fermatech.

The Protein A is immobilized on a solid phase. By "solid phase" is meant a non-aqueous matrix to which the Protein A can adhere. The solid phase of interest herein is generally one which comprises a glass, silica, agarose or polystyrene surface. The solid phase may be a purification column or a discontinuous phase of discrete particles. In preferred embodiments, the solid phase is a controlled pore glass column or a silicic acid column. In certain embodiments, the solid phase is coated with a reagent (such as glycerol) which is intended to prevent nonspecific adherence of contaminants to the solid phase.

The protein of interest herein is one which comprises a $C_H2/C_H3$ region and therefore is amenable to purification by Protein A chromatography. The term "$C_H2/C_H3$ region" when used herein refers to those amino acid residues in the Fc region of an immunoglobulin molecule which interact with Protein A. In preferred embodiments, the $C_H2/C_H3$ region comprises an intact $C_H2$ region followed by an intact $C_H3$ region, and most preferably comprises a Fc region of an immunoglobulin. Examples of $C_H2/C_H3$ region-containing proteins include antibodies, immunoadhesins and fusion proteins comprising a protein of interest fused to, or conjugated with, a $C_H2/C_H3$ region.

The "intermediate wash step" is a step performed after the protein of interest is loaded on the solid phase and adsorbed to the Protein A, but before the protein is recovered from the column. The intermediate wash step serves to remove contaminants nonspecifically bound to the solid phase, antibody and/or Protein A, without significantly eluting the protein of interest or Protein A from the solid phase. In the intermediate wash step, the solid phase is washed with the desired "intermediate wash buffer" (e.g. the intermediate wash buffer is passed through the Protein A column, where the solid phase is a column).

A "buffer" is a buffered solution that resists changes in pH by the action of its acid-base conjugate components.

An "equilibration buffer" herein is that used to prepare the solid phase (with immobilized Protein A) for loading the protein of interest. The equilibration buffer is preferably isotonic and commonly has a pH in the range from about 6 to about 8. The equilibration buffer of the example was 25 mM Tris, 25 mM NaCl, 5 mM EDTA, pH 7.1.

The "loading buffer" is that which is used to load the mixture of the $C_H2/C_H3$ region-containing protein and contaminant(s) onto the solid phase to which the Protein A is immobilized. Often, the equilibration and loading buffers are the same.

The "elution buffer" is used to elute the $C_H2/C_H3$ region-containing protein from the immobilized Protein A. Preferably the elution buffer has a low pH and thereby disrupts interactions between Protein A and the protein of interest. Preferably, the low pH elution buffer has a pH in the range from about 2 to about 5, most preferably in the range from about 3 to about 4. Examples of buffers that will control the pH within this range include phosphate, acetate, citrate and ammonium buffers, as well as combinations of these. The preferred such buffers are citrate and acetate buffers, most preferably sodium citrate or sodium acetate buffers. Other elution buffers are contemplated including high pH buffers (e.g. those having a pH of 9 or more) or buffers comprising a compound or composition such as $MgCl_2$ (2 mM) for eluting the protein of interest.

The "intermediate wash buffer" is the buffer used to remove contaminant(s), such as CHOP, from the immobilized Protein A without removing significant amounts of the protein of interest bound to the Protein A. The intermediate wash buffer preferably comprises (a) salt and detergent (e.g polysorbate); (b) salt and solvent (e.g. hexylene glycol); (c) high concentration salt (e.g. high molarity Tris buffer); or (d) salt and polymer (e.g. PEG).

A "salt" is a compound formed by the interaction of an acid and a base. The preferred salt herein is acetate (e.g. sodium acetate), citrate (e.g. sodium citrate), chloride (e.g. sodium chloride), sulphate (e.g. sodium sulphate), or a potassium salt.

As used herein, "solvent" refers to a liquid substance capable of dissolving or dispersing one or more other substances to provide a solution. The preferred solvent is an organic, non-polar solvent, such as ethanol, methanol, isopropanol, acetonitrile, hexylene glycol, propylene glycol, and 2,2-thiodiglycol.

The term "detergent" refers to nonionic surfactants such as polysorbates (e.g. polysorbates 20 or 80); poloxamers (e.g. poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; and the MONAQUAT™ series (Mona Industries, Inc., Paterson, N.J.), The preferred detergent is a polysorbate, such as polysorbate 20 (TWEEN 20®) or polysorbate 80 (TWEEN 80®).

A "polymer" herein is a molecule formed by covalent linkage of two or more monomers, where the monomers are not amino acid residues. Examples of polymers include polyethyl glycol, polypropyl glycol, and copolymers of ethylene and propylene glycol (e.g. Pluronics, PF68 etc). The preferred polymer is polyethylene glycol (PEG), e.g. PEG 400 and PEG 8000.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they retain, or are modified to comprise, a $C_H2/C_H3$ region as herein defined.

"Antibody fragments" comprise a portion of a full length antibody, generally the antigen binding or variable region thereof. Examples of antibody fragments include Fab, Fab', F(ab')$_2$, and Fv fragments; single-chain antibody molecules; diabodies; linear antibodies; and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature 256:495 (1975), or may be made by recombinant DNA methods (see, e.g., U.S. Pat. No. 4,816,567). The "monoclonal antibodies" may also be isolated from phage antibody libraries using the techniques described in Clackson et al., Nature 352:624–628 (1991) and Marks et al., J. Mol. Biol. 222:581–597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851–6855 (1984)).

The term "hypervariable region" when used herein refers to the amino acid residues of an antibody which are responsible for antigen-binding. The hypervariable region comprises amino acid residues from a "complementarity determining region" or "CDR" (i.e. residues 24–34 (L1), 50–56 (L2) and 89–97 (L3) in the light chain variable domain and 31–35 (H1), 50–65 (H2) and 95–102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (i.e. residues 26–32 (L1), 50–52 (L2) and 91–96 (L3) in the light chain variable domain and 26–32 (H1), and 96–101 (H3) in the heavy chain variable domain; Chothia and Lesk J. Mol. Biol. 196:901–917 (1987)). "Framework" or "FR" residues are those variable domain residues other than the hypervariable region residues as herein defined.

"Humanized" forms of non-human (e.g., murine) antibodies are chimeric antibodies which contain minimal sequence derived from non-human immunoglobulin. For the most part, humanized antibodies are human immunoglobulins (recipient antibody) in which hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al., Nature 321:522–525 (1986); Riechmann et al., Nature 332:323–329 (1988); and Presta, Curr. Op. Struct. Biol. 2:593–596 (1992).

As used herein, the term "immunoadhesin" designates antibody-like molecules which combine the "binding domain" of a heterologous "adhesin" protein (e.g. a receptor, ligand or enzyme) with the effector functions of an immunoglobulin constant domain. Structurally, the immunoadhesins comprise a fusion of the adhesin amino acid sequence with the desired binding specificity which is other than the antigen recognition and binding site (antigen combining site) of an antibody (i.e. is "heterologous") and an immunoglobulin constant domain sequence. The immunoglobulin constant domain sequence in the immunoadhesin is preferably derived from γ1, γ2, or γ4 heavy chains since immunoadhesins comprising these regions can be purified by Protein A chromatography (Lindmark et al., J. Immunol. Meth. 62:1–13 (1983)).

The term "ligand binding domain" as used herein refers to any native cell-surface receptor or any region or derivative thereof retaining at least a qualitative ligand binding of a corresponding native receptor. In a specific embodiment, the receptor is from a cell-surface polypeptide having an extracellular domain which is homologous to a member of the immunoglobulin supergenefamily. Other receptors, which are not members of the immunoglobulin supergenefamily but are nonetheless specifically covered by this definition, are receptors for cytokines, and in particular receptors with tyrosine kinase activity (receptor tyrosine kinases), members of the hematopoietin and nerve growth factor receptor superfamilies, and cell adhesion molecules, e.g. (E-, L- and P-) selectins.

The term "receptor binding domain" is used to designate any native ligand for a receptor, including cell adhesion molecules, or any region or derivative of such native ligand retaining at least a qualitative receptor binding ability of a corresponding native ligand. This definition, among others, specifically includes binding sequences from ligands for the above-mentioned receptors.

An "antibody-immunoadhesin chimera" comprises a molecule which combines at least one binding domain of an antibody (as herein defined) with at least one immunoadhesin (as defined in this application). Exemplary antibody-immunoadhesin chimeras are the bispecific CD4-IgG chimeras described in Berg et al., *PNAS (USA)* 88:4723–4727 (1991) and Chamow et al., *J. Immunol.* 153:4268 (1994).

"Trastuzumab" or "HERCEPTIN®" is a humanized anti-HER2 antibody comprising the light chain amino acid sequence of SEQ ID NO:1 and the heavy chain amino acid sequence of SEQ ID NO:2 or amino acid sequence variants thereof which retain the ability to bind HER2 and inhibit growth of tumor cells which overexpress HER2 (see U.S. Pat. No. 5,677,171; expressly incorporated herein by reference).

MODES FOR CARRYING OUT THE INVENTION

The process herein involves purifying a $C_H2/C_H3$ region-containing protein from contaminants by Protein A chromatography. In preferred embodiments, the protein to be purified using Protein A chromatography is an antibody, an immunoadhesin or a protein fused to, or conjugated with, a $C_H2/C_H3$ region. Techniques for generating such molecules will be discussed below.

1. Antibodies

The preferred protein to be purified according to the present invention is an antibody. Antibodies within the scope of the present invention include, but are not limited to: anti-HER2 antibodies including Trastuzumab (HERCEPTIN®) (Carter et al., *Proc. Natl. Acad. Sci. USA*, 89:4285–4289 (1992), U.S. Pat. No. 5,725,856); anti-CD20 antibodies such as chimeric anti-CD20 "C2B8" as in U.S. Pat. No. 5,736,137 (RITUXAN®), a chimeric or humanized variant of the 2H7 antibody as in U.S. Pat. No. 5,721,108, B1, or Tositumomab (BEXXAR®)); anti-IL-8 (St John et al., *Chest*, 103:932 (1993), and International Publication No. WO 95/23865); anti-VEGF antibodies including humanized and/or affinity matured anti-VEGF antibodies such as the humanized anti-VEGF antibody huA4.6.1 AVASTIN® (Kim et al., *Growth Factors*, 7:53–64 (1992), International Publication No. WO 96/30046, and WO 98/45331, published Oct. 15, 1998); anti-PSCA antibodies (WO01/40309); anti-CD40 antibodies, including S2C6 and humanized variants thereof (WO00/75348); anti-CD11a (U.S. Pat. No. 5,622,700, WO 98/23761, Steppe et al., *Transplant Intl.* 4:3–7 (1991), and Hourmant et al., *Transplantation* 58:377–380 (1994)); anti-IgE (Presta et al., *J. Immunol.* 151:2623–2632 (1993), and International Publication No. WO 95/19181); anti-CD18 (U.S. Pat. No. 5,622,700, issued Apr. 22, 1997, or as in WO 97/26912, published Jul. 31, 1997); anti-IgE (including E25, E26 and E27; U.S. Pat. No. 5,714,338, issued Feb. 3, 1998 or U.S. Pat. No. 5,091,313, issued Feb. 25, 1992, WO 93/04173 published Mar. 4, 1993, or International Application No. PCT/US98/13410 filed Jun. 30, 1998, U.S. Pat. No. 5,714,338); anti-Apo-2 receptor antibody (WO 98/51793 published Nov. 19, 1998); anti-TNF-α antibodies including cA2 (REMICADE®), CDP571 and MAK-195 (See, U.S. Pat. No. 5,672,347 issued Sep. 30, 1997, Lorenz et al. *J. Immunol.* 156(4):1646–1653 (1996), and Dhainaut et al. *Crit. Care Med.* 23(9):1461–1469 (1995)); anti-Tissue Factor (TF) (European Patent No. 0 420 937 B1 granted Nov. 9, 1994); anti-human $\alpha_4\beta_7$ integrin (WO 98/06248 published Feb. 19, 1998); anti-EGFR (chimerized or humanized 225 antibody as in WO 96/40210 published Dec. 19, 1996); anti-CD3 antibodies such as OKT3 (U.S. Pat. No. 4,515,893 issued May 7, 1985); anti-CD25 or anti-tac antibodies such as CHI-621 (SIMULECT®) and (ZENAPAX®) (See U.S. Pat. No. 5,693,762 issued Dec. 2, 1997); anti-CD4 antibodies such as the cM-7412 antibody (Choy et al. *Arthritis Rheum* 39(1):52–56 (1996)); anti-CD52 antibodies such as CAMPATH-1H (Riechmann et al. *Nature* 332:323–337 (1988)); anti-Fc receptor antibodies such as the M22 antibody directed against FcγRI as in Graziano et al. *J. Immunol.* 155(10):4996–5002 (1995); anti-carcinoembryonic antigen (CEA) antibodies such as hMN-14 (Sharkey et al. *Cancer Res.* 55(23Suppl): 5935s–5945s (1995); antibodies directed against breast epithelial cells including huBrE-3, hu-Mc 3 and CHL6 (Ceriani et al. *Cancer Res.* 55(23): 5852s–5856s (1995); and Richman et al. *Cancer Res.* 55(23 Supp): 5916s–5920s (1995)); antibodies that bind to colon carcinoma cells such as C242 (Litton et al. *Eur J. Immunol.* 26(1):1–9 (1996)); anti-CD38 antibodies, e.g. AT 13/5 (Ellis et al. *J. Immunol.* 155(2):925–937 (1995)); anti-CD33 antibodies such as Hu M195 (Jurcic et al. *Cancer Res* 55(23 Suppl):5908s–5910s (1995) and CMA-676 or CDP771; anti-CD22 antibodies such as LL2 or LymphoCide (Juweid et al. *Cancer Res* 55(23 Suppl):5899s–5907s (1995)); anti-EpCAM antibodies such as 17-1A (PANOREX®); anti-GpIIb/IIIa antibodies such as abciximab or c7E3 Fab (REOPRO®); anti-RSV antibodies such as MEDI-493 (SYNAGIS®); anti-CMV antibodies such as PROTOVIR®; anti-HIV antibodies such as PRO542; anti-hepatitis antibodies such as the anti-Hep B antibody OSTAVIR®; anti-CA 125 antibody OvaRex; anti-idiotypic GD3 epitope antibody BEC2; anti-αvβ3 antibody VITAXIN®; anti-human renal cell carcinoma antibody such as ch-G250; ING-1; anti-human 17-1A antibody (3622W94); anti-human colorectal tumor antibody (A33); anti-human melanoma antibody R24 directed against GD3 ganglioside; anti-human squamous-cell carcinoma (SF-25); and anti-human leukocyte antigen (HLA) antibodies such as Smart ID10 and the anti-HLA DR antibody Oncolym (Lym-1). The preferred target antigens for the antibody herein are: HER2 receptor, VEGF, IgE, CD20, CD11a, and CD40.

Aside from the antibodies specifically identified above, the skilled practitioner could generate antibodies directed against an antigen of interest, e.g., using the techniques described below.

(i) Antigen Selection and Preparation

The antibody herein is directed against an antigen of interest. Preferably, the antigen is a biologically important polypeptide and administration of the antibody to a mammal suffering from a disease or disorder can result in a therapeutic benefit in that mammal. However, antibodies directed against nonpolypeptide antigens (such as tumor-associated glycolipid antigens; see U.S. Pat. No. 5,091,178) are also contemplated. Where the antigen is a polypeptide, it may be a transmembrane molecule (e.g. receptor) or ligand such as a growth factor. Exemplary antigens include those proteins described in section (3) below. Exemplary molecular targets for antibodies encompassed by the present invention include CD proteins such as CD3, CD4, CD8, CD19, CD20, CD22 and CD34; members of the ErbB receptor family such as the EGF receptor, HER2, HER3 or HER4 receptor; cell adhesion molecules such as LFA-1, Mac1, p150,95, VLA-4, ICAM-1, VCAM and αv/β3 integrin including either α or β subunits thereof (e.g. anti-CD11a, anti-CD18 or anti-CD11b antibodies); growth factors such as VEGF; IgE; blood group antigens; flk2/flt3 receptor; obesity (OB) receptor; mpl receptor; CTLA-4; protein C, or any of the other antigens mentioned herein.

Soluble antigens or fragments thereof, optionally conjugated to other molecules, can be used as immunogens for generating antibodies. For transmembrane molecules, such as receptors, fragments of these (e.g. the extracellular domain of a receptor) can be used as the immunogen. Alternatively, cells expressing the transmembrane molecule can be used as the immunogen. Such cells can be derived from a natural source (e.g. cancer cell lines) or may be cells which have been transformed by recombinant techniques to express the transmembrane molecule.

Other antigens and forms thereof useful for preparing antibodies will be apparent to those in the art.

(ii) Polyclonal Antibodies

Polyclonal antibodies are preferably raised in animals by multiple subcutaneous (sc) or intraperitoneal (ip) injections of the relevant antigen and an adjuvant. It may be useful to conjugate the antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 µg or 5 µg of the protein or conjugate (for rabbits or mice, respectively) with 3 volumes of Freund's complete adjuvant and injecting the solution intradermally at multiple sites. One month later the animals are boosted with ⅕ to ⅒ the original amount of antigen or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(iii) Monoclonal Antibodies

Monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster or macaque monkey, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp.59–103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8–653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51–63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp.59–103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, Protein A-Sepharose, hydroxylapatite chromatography, gel electrophoresis, dialysis, or affinity chromatography. Preferably the Protein A chromatography procedure described herein is used.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells.

The DNA also may be modified, for example, by substituting the coding sequence for human heavy- and light-chain constant domains in place of the homologous murine sequences (U.S. Pat. No. 4,816,567; Morrison, et al., *Proc. Nat Acad. Sci. USA*, 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

In a further embodiment, monoclonal antibodies can be isolated from antibody phage libraries generated using the techniques described in McCafferty et al., *Nature*, 348:552–554 (1990). Clackson et al., *Nature*, 352:624–628 (1991) and Marks et al., *J. Mol. Biol.*, 222:581–597 (1991) describe the isolation of murine and human antibodies, respectively, using phage libraries. Subsequent publications describe the production of high affinity (nM range) human antibodies by chain shuffling (Marks et al., *Bio/Technology*, 10:779–783 (1992)), as well as combinatorial infection and in vivo recombination as a strategy for constructing very large phage libraries (Waterhouse et a., *Nuc. Acids. Res.*, 21:2265–2266 (1993)). Thus, these techniques are viable alternatives to traditional hybridoma techniques for isolation of monoclonal antibodies.

(iv) Humanized and Human Antibodies

A humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522–525 (1986); Riechmann et al., *Nature*, 332:323–327 (1988); Verhoeyen et al., *Science*, 239:1534–1536 (1988)), by substituting rodent CDRs or CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human FR for the humanized antibody (Sims et al., *J. Immunol.*, 151:2296 (1993)). Another method uses a particular framework derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immnol.*, 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255–258 (1993); Bruggermann et al., *Year in Immuno.*, 7:33 (1993); and Duchosal et al. *Nature* 355:258 (1992). Human antibodies can also be derived from phage-display libraries (Hoogenboom et al., *J. Mol. Biol.*, 227:381 (1991); Marks et al., *J. Mol. Biol.*, 222:581–597 (1991); Vaughan et al. *Nature Biotech* 14:309 (1996)).

(v) Antibody Fragments

Various techniques have been developed for the production of antibody fragments. Traditionally, these fragments were derived via proteolytic digestion of intact antibodies (see, e.g., Morimoto et al., *Journal of Biochemical and Biophysical Methods* 24:107–117 (1992) and Brennan et al., *Science*, 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., Bio/Technology 10:163–167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185.

(vi) Multispecific Antibodies

Multispecific antibodies have binding specificities for at least two different antigens. While such molecules normally will only bind two antigens (i.e. bispecific antibodies, BsAbs), antibodies with additional specificities such as trispecific antibodies are encompassed by this expression when used herein.

Methods for making bispecific antibodies are known in the art. Traditional production of full length bispecific antibodies is based on the coexpression of two immunoglobulin heavy chain-light chain pairs, where the two chains have different specificities (Millstein et al., *Nature*, 305:537–539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.*, 10:3655–3659 (1991).

According to another approach described in WO96/27011, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217–225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.*, 148(5):1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444–6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994). Alternatively, the antibodies can be "linear antibodies" as described in Zapata et al. *Protein Eng.* 8(10):1057–1062 (1995). Briefly, these antibodies comprise a pair of tandem Fd segments ($V_H$-$C_H1$-$V_H$-$C_H1$) which form a pair of antigen binding regions. Linear antibodies can be bispecific or monospecific.

Antibodies with more than two valencies are contemplated. For example, trispecific antibodies can be prepared. Tutt et al. *J. Immunol.* 147: 60 (1991).

2. Immunoadhesins

The simplest and most straightforward immunoadhesin design combines the binding domain(s) of the adhesin (e.g. the extracellular domain (ECD) of a receptor) with the hinge and Fc regions of an immunoglobulin heavy chain. Ordinarily, when preparing the immunoadhesins of the present invention, nucleic acid encoding the binding domain of the adhesin will be fused C-terminally to nucleic acid encoding the N-terminus of an immunoglobulin constant domain sequence, however N-terminal fusions are also possible.

Typically, in such fusions the encoded chimeric polypeptide will retain at least functionally active hinge, $C_H2$ and $C_H3$ domains of the constant region of an immunoglobulin heavy chain. Fusions are also made to the C-terminus of the Fc portion of a constant domain, or immediately N-terminal to the $C_H1$ of the heavy chain or the corresponding region of the light chain. The precise site at which the fusion is made is not critical; particular sites are well known and may be selected in order to optimize the biological activity, secretion, or binding characteristics of the immunoadhesin.

In a preferred embodiment, the adhesin sequence is fused to the N-terminus of the Fc domain of immunoglobulin $G_1$ ($IgG_1$). It is possible to fuse the entire heavy chain constant region to the adhesin sequence. However, more preferably, a sequence beginning in the hinge region just upstream of the papain cleavage site which defines IgG Fc chemically (i.e. residue 216, taking the first residue of heavy chain constant region to be 114), or analogous sites of other immunoglobulins is used in the fusion. In a particularly preferred embodiment, the adhesin amino acid sequence is fused to (a) the hinge region and $C_H2$ and $C_H3$ or (b) the $C_H1$, hinge, $C_H2$ and $C_H3$ domains, of an IgG heavy chain.

For bispecific immunoadhesins, the immunoadhesins are assembled as multimers, and particularly as heterodimers or heterotetramers. Generally, these assembled immunoglobulins will have known unit structures. A basic four chain structural unit is the form in which IgG, IgD, and IgE exist. A four chain unit is repeated in the higher molecular weight immunoglobulins; IgM generally exists as a pentamer of four basic units held together by disulfide bonds. IgA globulin, and occasionally IgG globulin, may also exist in multimeric form in serum. In the case of multimer, each of the four units may be the same or different.

Various exemplary assembled immunoadhesins within the scope herein are schematically diagrammed below:

(a) $AC_L$-$AC_L$;
(b) $AC_H$-($AC_H$, $AC_L$-$AC_H$, $AC_L$-$V_H C_H$, or $V_L C_L$-$AC_H$);
(c) $AC_L$-$AC_H$-($AC_L$-$AC_H$, $AC_L$-$V_H C_H$, $V_L C_L$-$AC_H$, or $V_L C_L$-$V_H C_H$)
(d) $AC_L$-$V_H C_H$-($AC_H$, or $AC_L$-$V_H C_H$, or $V_L C_L$-$AC_H$);
(e) $V_L C_L$-$AC_H$-($AC_L$-$V_H C_H$, or $V_L C_L$-$AC_H$); and
(f) $(A-Y)_n$-$(V_L C_L$-$V_H C_H)_2$, wherein each A represents identical or different adhesin amino acid sequences;

$V_L$ is an immunoglobulin light chain variable domain;
$V_H$ is an immunoglobulin heavy chain variable domain;
$C_L$ is an immunoglobulin light chain constant domain;
$C_H$ is an immunoglobulin heavy chain constant domain;
n is an integer greater than 1;
Y designates the residue of a covalent cross-linking agent.

In the interests of brevity, the foregoing structures only show key features; they do not indicate joining (J) or other domains of the immunoglobulins, nor are disulfide bonds shown. However, where such domains are required for binding activity, they shall be constructed to be present in the ordinary locations which they occupy in the immunoglobulin molecules.

Alternatively, the adhesin sequences can be inserted between immunoglobulin heavy chain and light chain sequences, such that an immunoglobulin comprising a chimeric heavy chain is obtained. In this embodiment, the adhesin sequences are fused to the 3' end of an immunoglobulin heavy chain in each arm of an immunoglobulin, either between the hinge and the $C_H2$ domain, or between the $C_H2$ and $C_H2$ domains. Similar constructs have been reported by Hoogenboom, et al., *Mol. Immunol.* 28:1027–1037 (1991).

Although the presence of an immunoglobulin light chain is not required in the immunoadhesins of the present invention, an immunoglobulin light chain might be present either covalently associated to an adhesin-immunoglobulin heavy chain fusion polypeptide, or directly fused to the adhesin. In the former case, DNA encoding an immunoglobulin light chain is typically coexpressed with the DNA encoding the adhesin-immunoglobulin heavy chain fusion protein. Upon secretion, the hybrid heavy chain and the light chain will be covalently associated to provide an immunoglobulin-like structure comprising two disulfide-linked immunoglobulin heavy chain-light chain pairs. Methods suitable for the preparation of such structures are, for example, disclosed in U.S. Pat. No. 4,816,567, issued Mar. 28, 1989.

Immunoadhesins are most conveniently constructed by fusing the cDNA sequence encoding the adhesin portion in-frame to an immunoglobulin cDNA sequence. However, fusion to genomic immunoglobulin fragments can also be used (see, e.g. Aruffo et al., *Cell* 61:1303–1313 (1990); and Stamenkovic et al., *Cell* 66:1133–1144 (1991)). The latter type of fusion requires the presence of Ig regulatory sequences for expression. cDNAs encoding IgG heavy-chain constant regions can be isolated based on published sequences from cDNA libraries derived from spleen or peripheral blood lymphocytes, by hybridization or by polymerase chain reaction (PCR) techniques. The cDNAs encoding the "adhesin" and the immunoglobulin parts of the immunoadhesin are inserted in tandem into a plasmid vector that directs efficient expression in the chosen host cells.

3. Other $C_H2/C_H3$ Region-Containing Proteins

In other embodiments, the protein to be purified is one which is fused to, or conjugated with, a $C_H2/C_H3$ region. Such fusion proteins may be produced so as to increase the serum half-life of the protein and/or to facilitate purification of the protein by Protein A chromatography. Examples of biologically important proteins which can be conjugated this way include renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; Protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1–3)-IGF-I (brain IGF-I), insulin-like growth factor binding proteins; CD proteins such as CD3, CD4, CD8, CD19 and CD20; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as HER2, HER3 or HER4 receptor; and fragments of any of the above-listed polypeptides.

4. Protein Purification

The protein to be purified using the method described herein is generally produced using recombinant techniques. Methods for producing recombinant proteins are described, e.g., in U.S. Pat Nos. 5,534,615 and 4,816,567, specifically incorporated herein by reference. In preferred embodiments, the protein of interest is produced in a CHO cell (see, e.g. WO 94/11026). Examples of proteins which can be purified using the process described herein have been described above.

When using recombinant techniques, the protein can be produced intracellularly, in the periplasmic space, or directly secreted into the medium. If the protein is produced intracellularly, as a first step, the particulate debris, either host cells or lysed fragments, is removed, for example, by centrifugation or ultrafiltration. Where the protein is secreted into the medium, the recombinant host cells may be separated from the cell culture medium by tangential flow filtration, for example.

Protein A immobilized on a solid phase is used to purify the $C_H2/C_H3$ region-containing protein. The solid phase is preferably a column comprising a glass, silica, agarose or polystyrene surface for immobilizing the Protein A. Preferably, the solid phase is a controlled pore glass column or a silicic acid column. Sometimes, the column has been coated with a reagent, such as glycerol, in an attempt to prevent nonspecific adherence to the column. The PROSEP A™ column, commercially available from Bioprocessing Limited, is an example of a Protein A controlled pore glass column which is coated with glycerol. Other examples of columns contemplated herein include the POROS 50 A™ (polystyrene) column or rProtein A SEPHAROSE FAST FLOW™ (agarose) column.

The solid phase for the Protein A chromatography is equilibrated with a suitable buffer. For example, the equilibration buffer may be 25 mM Tris, 25 mM NaCl, 5 mM EDTA, pH 7.1.

The contaminated preparation derived from the recombinant host cells is loaded on the equilibrated solid phase using a loading buffer which may be the same as the equilibration buffer. As the contaminated preparation flows through the solid phase, the protein is adsorbed to the immobilized Protein A and other contaminants (such as Chinese Hamster Ovary Proteins, CHOP, where the protein is produced in a CHO cell) may bind nonspecifically to the solid phase.

The next step performed sequentially entails removing the contaminants bound to the solid phase, antibody and/or Protein A, by washing the solid phase in an intermediate wash step. After loading, the solid phase may be equilibrated with equilibration buffer before beginning the intermediate wash step.

The intermediate wash buffer may comprise salt and a further compound, where the further compound is (a) detergent (preferably polysorbate, e.g. polysorbate 20 or polysorbate 80); (b) solvent (preferably hexylene glycol); and (c) polymer (preferably PEG).

The salt employed may be selected based on the protein of interest, but preferably is acetate (e.g. sodium acetate), especially where the antibody is an anti-HER2 antibody such as Trastuzumab; or citrate (e.g. sodium citrate), especially where the antibody is an anti-IgE antibody such as E26.

The amounts of the salt and further compound in the composition are such that the combined amount elutes the contaminant(s), without substantially removing the protein of interest. Preferred salt concentrations in such wash buffers are from about 0.1 to about 2M, and more preferably from about 0.2M to about 0.6M. Useful detergent concentrations are from about 0.01 to about 5%, more preferably from about 0.1 to 1%, and most preferably about 0.5%, e.g. where the detergent is polysorbate. Exemplary solvent concentrations are from about 1% to 40%, preferably from about 5 to about 25%. For instance, in the examples herein, the preferred concentration of the solvent (hexylene glycol) for E26 was about 20%, whereas for Trastuzumab the preferred concentration of the solvent (again hexylene glycol) was about 10%. Where the further compound is a polymer (e.g. PEG 400 or PEG 8000), the concentration thereof may, for example, be from about 1% to about 20%, preferably from about 5% to about 15%.

In another embodiment, the intermediate wash step involves the use of a highly concentrated buffer solution, e.g. a buffer at a concentration of greater than about 0.8M, e.g. up to about 2M, and preferably in the range from about 0.8M to about 1.5M, most preferably about 1M. In this embodiment, the buffer is preferably a Tris buffer, such as Tris acetate.

The pH of the intermediate wash buffer is preferably from about 4 to about 8, more preferably from about 4.5 to about 5.5, and most preferably about 5.0. In another preferred embodiment, the pH is about 7.0.

Following the intermediate wash step of the preceding paragraph, the protein of interest is recovered from the column. This is normally achieved using a suitable elution buffer. The protein may, for example, be eluted from the column using an elution buffer having a low pH, e.g. in the range from about 2 to about 5, and preferably in the range from about 2.5 to about 3.5. Examples of elution buffers for this purpose include citrate or acetate buffers.

The eluted protein preparation may be subjected to additional purification steps either prior to, or after, the Protein A chromatography step. Exemplary further purification steps include hydroxylapatite chromatography; dialysis; affinity chromatography using an antibody to capture the protein; hydrophobic interaction chromatography (HIC); ammonium sulphate precipitation; anion or cation exchange chromatography; ethanol precipitation; reverse phase HPLC; chromatography on silica; chromatofocusing; and gel filtration. In the examples herein, the Protein A chromatography step is followed by downstream cation exchange (SP-Sepharose) and anion exchange (Q-Sepharose) purification steps.

The protein thus recovered may be formulated in a pharmaceutically acceptable carrier and is used for various diagnostic, therapeutic or other uses known for such molecules.

The following examples are offered by way of illustration and not by way of limitation. The disclosures of all citations in the specification are expressly incorporated herein by reference.

EXAMPLE 1

Intermediate Wash Solutions

The anti-HER2 antibody Trastuzumab (FIGS. 1A–B; HERCEPTIN®), anti-IgE antibody (E26; U.S. Pat. No. 5,994,511, Lowman et al.) and humanized anti-CD11a antibody (XANELIM®; U.S. Pat. No. 6,037,454) were recombinantly produced in Chinese Hamster Ovary (CHO) cells and purified by Protein A chromatography as a first chromatographic step to remove contaminating CHO proteins (CHOP). However, CHOP tends to binding non-specifically to ProSepA, the resin used for this step. ProSep A has the antibody-binding Protein A immoblized on glycerol-coated controlled-pore glass. Although the glycerol coat reduces non-specific binding, some CHOP still adheres to the resin's glass backbone. During the elution phase of the Protein A operation, any non-specifically bound CHOP will co-elute with the antibody, compromising the purity of the product pool. To remove this CHOP before the elution phase, U.S. Pat. Nos. 6,127,526 and 6,333,398 (Blank, G.) exemplify an intermediate wash step using tetramethylammonium chloride (TMAC) to remove CHOP. Although TMAC is effective at removing non-specifically bound CHOP, it is difficult to handle and dispense, is toxic, requires costly disposal as a hazardous waste, and is corrosive at high concentration and low pH. The following study shows that alternative wash compositions, without the drawbacks of TMAC, can be used in an intermediate wash step. The other buffers (equilibration, load, elution and regeneration buffers) were as in the Example in U.S. Pat. Nos. 6,127,526 and 6,333,398.

A wide variety of "intermediate wash buffers" were screened with regard to the anti-IgE antibody E26, the anti-HER2 antibody Trastuzumab, and the anti-CD11a antibody XANELIM™. The classes of wash buffers were: (a) detergent and salt; (b) solvent and salt; (c) polymer and salt; (d) high concentration buffer; and (e) urea.

The protein yield, CHOP removal, and protein aggregation in the Protein A pools were determined for each of the intermediate wash buffers. For all runs, yield was greater than 94%, except the intermediate wash solution with 20% hexylene glycol where the protein was Trastuzumab. CHOP removal achieved with the various intermediate wash buffers is depicted in FIGS. 2–6. Protein aggregation as determined by size exclusion chromatography was less than 1.5% for all runs.

The preferred intermediate wash buffers, taking into consideration CHOP clearance, final protein yield and ease of use, were: (a) polysorbate/salt; (b) hexylene glycol/salt; and (c) high concentration Tris buffer. The polysorbate/salt intermediate wash buffer was selected for further studies.

EXAMPLE 2

Alteration of the Intermediate Wash Buffer

The effect of (a) salt type and concentration, (b) polysorbate concentration, and (c) pH of the intermediate wash buffer on CHOP removal was evaluated. The antibodies were the anti-IgE antibody E26, and the anti-HER2 antibody Trastuzumab.

FIG. 7 depicts the effect of salt type and concentration on CHOP removal. For E26, CHOP level in the elution pool was not significantly affected by concentration of citrate or sulphate in the wash solution. For Trastuzumab, CHOP level in the elution pool was affected by the concentration of salt in the intermediate wash buffer. Preferred concentrations of the salt were from about 0.3 to about 0.6M.

The effect of polysorbate concentration on CHOP level in the elution pool was also evaluated. As shown in FIG. 8, as the concentration of polysorbate in the intermediate wash buffer increased, the amount of CHOP contamination decreased. The preferred concentration of polysorbate is about 0.5% to about 1%.

The effect of pH on CHOP was also assessed and the results of these experiments are shown in FIG. 9. A lower pH resulted in less CHOP contamination in the eluted protein. The preferred pH is about 5.

EXAMPLE 3

Downstream Performance

The downstream performance in terms of CHOP removal, yield, etc (SDS-PAGE, HPLC-IEC, size exclusion chromatography (SEC), and protein A leaching), were determined for E26 and Trastuzumab. The downstream purification steps were cation exchange chromatography (SP-Sepharose) and anion exchange chromatography (Q-Sepharose).

For E26, the intermediate wash buffers were: (a) 0.5% polysorbate 20/0.2M sodium citrate, (b) 20% hexylene glycol/0.2M sodium citrate, and (c) 1M Tris acetate. The results are shown in the following Table.

TABLE 1

E26 Downstream

| | CHOP (ppm) | | | | |
|---|---|---|---|---|---|
| Step | TMAC | Polys/Salt | Hex Gly/Salt | TrisOAc | Equil |
| Pro A | 320 | 260 | 230 | 310 | 600 |
| SP-Seph | 50 | 40 | 30 | 40 | 90 |
| Q-Seph | <1 | <1 | <1 | <1 | 4 |
| Overall % Yield: | 74 | 72 | 67 | 73 | 72 |

For Trastuzumab, the intermediate wash buffers were: (a) 0.5% polysorbate 20/0.5M sodium acetate, (b) 10% hexylene glycol/0.5M sodium acetate, and (c) 1M Tris acetate. The results are summarized in the Tables below.

TABLE 2

Trastuzumab Downstream

| | CHOP (ppm) | | | | |
|---|---|---|---|---|---|
| Step | TMAC | Polys/Salt | Hex Gly/Salt | TrisOAc | Equil |
| Pro A | 390 | 490 | 460 | 560 | 1540 |
| SP-Seph | 45 | 40 | 40 | 50 | 70 |
| Q-Seph* | <2 | <2 | <1 | <1 | 6 |
| Overall % yield: | 66 | 66 | 66 | 65 | 69 |

*Concentrated Q-Seph pool > 25 mg/ml

TABLE 3

Trastuzumab Downstream-Contribution of polysorbate 20 and salt

| | CHOP (ppm) | | | | |
|---|---|---|---|---|---|
| Step | TMAC | Polys/NaOAc | Polys | NaOAc | Equil |
| Pro A | 449 | 386 | 1328 | 628 | 2130 |
| SP-Seph | 12 | 13 | 13 | 22 | 24 |
| Q-Seph | <1 | <1 | <3 | 4 | 4 |
| Overall % yield: | 84 | 84 | 69* | 83 | 84 |

*Low yield (83%) at Protein A step

The yields and CHOP removal were similar for the two antibodies tested. Polysorbate, hexylene glycol and Tris showed good CHOP clearance and yield after Protein A chromatography and subsequent ion exchange chromatography steps.

Size Exclusion Chromatography (SEC) for measuring percentage aggregate and SDS-PAGE were performed on Q-Sepharose pools. Ion Exchange analysis (IEX) for measuring percent main peak, and SEC for evaluating aggregation were performed on Protein A and SP-Sepharose pools. For both Trastuzumab and E26, the assays showed similar results between the positive control (TMAC) and the alternative intermediate wash buffers.

EXAMPLE 4

Column Re-Use

The purpose of this experiment was to determine whether polysorbate 20 in the intermediate wash buffer affects resin lifetime. Buffers (equilibration, polysorbate 20 intermediate wash, elution and regeneration) were recycled on a 6.84 ml column (0.66 cm×20 cm) over 400 cycles. A HER2 breakthrough curve is performed every 50 cycles to determine resin binding capacity. The current specification for maximum binding capacity is 20 grams of antibody per liter of resin. A drop in binding capacity with increasing cycles would indicate that polysorbate 20 reduces resin lifetime. This experiment demonstrated that polysorbate 20 does not reduce resin lifetime. Actual re-use has been completed for 140 cycles and no change in yield has been seen.

What is claimed is:

1. A method for purifying a protein, which comprises a $C_H2/C_H3$ region, from a contaminated solution thereof by Protein A chromatography comprising:
   (a) adsorbing the protein from said contaminated solution to Protein A immobilized on a solid phase;
   (b) removing contaminants by washing the solid phase with a composition comprising detergent and salt at about pH 4.5 to about 5.5; and
   (c) recovering the protein from the solid phase with an elution buffer having a pH in the range from about 2 to about 5.

2. The method of claim 1 wherein the solid phase comprises silica, glass, agarose, or polystyrene.

3. The method of claim 2 wherein the solid phase. comprises silica or glass.

4. The method of claim 1 wherein the protein is an antibody or an immunoadhesin.

5. The method of claim 1 wherein the protein is an antibody.

6. The method of claim 5 wherein the antibody binds an antigen selected from the group consisting of HER2, vascular endothelial growth factor (VEGF), IgE, CD20, CD40, CD11a, tissue factor (TF), prostate stem cell antigen (PSCA), interleukin-8 (IL-8), epidermal growth factor receptor (EGER), HER3, HER4, α4β7 and α5β3.

7. The method of claim 5 wherein the antibody is an anti-HER2 antibody.

8. The method of claim 5 wherein the antibody is an anti-IgE antibody.

9. The method of claim 1 wherein the detergent is polysorbate.

10. The method of claim 9 wherein the concentration of the polysorbate in the composition is from about 0.1 to about 1%.

11. The method of claim 1 wherein the salt is acetate or citrate.

12. The method of claim 1 wherein the concentration of the salt in the composition is from about 0.2 to about 0.6 M.

13. A method for purifying a protein, which comprises a $C_H2/C_H3$ region, from a contaminated solution thereof by Protein A chromatography comprising:
   (a) adsorbing the protein to Protein A immobilized on a solid phase;
   (b) removing contaminants by washing the solid phase with a composition comprising a buffer at a concentration of greater than about 0.8M; and
   (c) recovering the protein from the solid phase.

14. The method of claim 13 wherein the buffer is Tris acetate.

15. The method of claim 14 wherein the concentration of the Tris acetate buffer is from about 0.8 to about 1.5 M.

16. A method for purifying a protein, which comprises a $C_H2/C_H3$ region, from a contaminated solution thereof by Protein A chromatography comprising:
   (a) adsorbing the protein to Protein A immobilized on a solid phase;
   (b) removing contaminants by washing the solid phase with a composition comprising salt and a solvent selected from the group consisting of ethanol, methanol, isopropanol, acetonitrile, hexylene glycol, propylene glycol, and 2,2-thiodiglycol; and
   (c) recovering the protein from the solid phase.

17. The method of claim 16 wherein the solvent is hexylene glycol.

18. A method for purifying a protein, which comprises a $C_H2/C_H3$ region, from a contaminated solution thereof by Protein A chromatography comprising:
   (a) adsorbing the protein to Protein A immobilized on a solid phase;
   (b) removing contaminants by washing the solid phase with a composition comprising salt and a polymer selected from the group consisting of polyethylene glycol, polypropyl glycol, and copolymers of ethylene and propylene glycol; and
   (c) recovering the protein from the solid phase.

19. The method of claim 18 wherein the polymer is polyethylene glycol.

* * * * *

SEQUENCE LISTING

<160> NUMBER OF SEQ ID NOS: 2

<210> SEQ ID NO 1
<211> LENGTH: 214
<212> TYPE: PRT
<213> ORGANISM: Artificial sequence
<220> FEATURE:
<223> OTHER INFORMATION: Sequence is synthesized.

<400> SEQUENCE: 1

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Val Asn
                20                  25                  30

Thr Ala Val Ala Trp Tyr Gln Gln Lys Pro Gly Lys Ala Pro Lys
                35                  40                  45

Leu Leu Ile Tyr Ser Ala Ser Phe Leu Tyr Ser Gly Val Pro Ser
                50                  55                  60

Arg Phe Ser Gly Ser Arg Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

His Tyr Thr Thr Pro Pro Thr Phe Gly Gln Gly Thr Lys Val Glu
                95                 100                 105

Ile Lys Arg Thr Val Ala Ala Pro Ser Val Phe Ile Phe Pro Pro
               110                 115                 120

Ser Asp Glu Gln Leu Lys Ser Gly Thr Ala Ser Val Val Cys Leu
               125                 130                 135

Leu Asn Asn Phe Tyr Pro Arg Glu Ala Lys Val Gln Trp Lys Val
               140                 145                 150

Asp Asn Ala Leu Gln Ser Gly Asn Ser Gln Glu Ser Val Thr Glu
               155                 160                 165

Gln Asp Ser Lys Asp Ser Thr Tyr Ser Leu Ser Ser Thr Leu Thr
               170                 175                 180

Leu Ser Lys Ala Asp Tyr Glu Lys His Lys Val Tyr Ala Cys Glu
               185                 190                 195

Val Thr His Gln Gly Leu Ser Ser Pro Val Thr Lys Ser Phe Asn
               200                 205                 210

Arg Gly Glu Cys

<210> SEQ ID NO 2
<211> LENGTH: 449
<212> TYPE: PRT
<213> ORGANISM: Artificial sequence
<220> FEATURE:
<223> OTHER INFORMATION: Sequence is synthesized.

<400> SEQUENCE: 2

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Asn Ile Lys
                20                  25                  30

Asp Thr Tyr Ile His Trp Val Arg Gln Ala Pro Gly Lys Gly Leu
                35                  40                  45

Glu Trp Val Ala Arg Ile Tyr Pro Thr Asn Gly Tyr Thr Arg Tyr
                50                  55                  60

-continued

```
Ala Asp Ser Val Lys Gly Arg Phe Thr Ile Ser Ala Asp Thr Ser
             65                  70                  75
Lys Asn Thr Ala Tyr Leu Gln Met Asn Ser Leu Arg Ala Glu Asp
             80                  85                  90
Thr Ala Val Tyr Tyr Cys Ser Arg Trp Gly Asp Gly Phe Tyr
             95                 100                 105
Ala Met Asp Tyr Trp Gly Gln Gly Thr Leu Val Thr Val Ser Ser
            110                 115                 120
Ala Ser Thr Lys Gly Pro Ser Val Phe Pro Leu Ala Pro Ser Ser
            125                 130                 135
Lys Ser Thr Ser Gly Gly Thr Ala Ala Leu Gly Cys Leu Val Lys
            140                 145                 150
Asp Tyr Phe Pro Glu Pro Val Thr Val Ser Trp Asn Ser Gly Ala
            155                 160                 165
Leu Thr Ser Gly Val His Thr Phe Pro Ala Val Leu Gln Ser Ser
            170                 175                 180
Gly Leu Tyr Ser Leu Ser Ser Val Val Thr Val Pro Ser Ser Ser
            185                 190                 195
Leu Gly Thr Gln Thr Tyr Ile Cys Asn Val Asn His Lys Pro Ser
            200                 205                 210
Asn Thr Lys Val Asp Lys Lys Val Glu Pro Lys Ser Cys Asp Lys
            215                 220                 225
Thr His Thr Cys Pro Pro Cys Pro Ala Pro Glu Leu Leu Gly Gly
            230                 235                 240
Pro Ser Val Phe Leu Phe Pro Pro Lys Pro Lys Asp Thr Leu Met
            245                 250                 255
Ile Ser Arg Thr Pro Glu Val Thr Cys Val Val Val Asp Val Ser
            260                 265                 270
His Glu Asp Pro Glu Val Lys Phe Asn Trp Tyr Val Asp Gly Val
            275                 280                 285
Glu Val His Asn Ala Lys Thr Lys Pro Arg Glu Glu Gln Tyr Asn
            290                 295                 300
Ser Thr Tyr Arg Val Val Ser Val Leu Thr Val Leu His Gln Asp
            305                 310                 315
Trp Leu Asn Gly Lys Glu Tyr Lys Cys Lys Val Ser Asn Lys Ala
            320                 325                 330
Leu Pro Ala Pro Ile Glu Lys Thr Ile Ser Lys Ala Lys Gly Gln
            335                 340                 345
Pro Arg Glu Pro Gln Val Tyr Thr Leu Pro Pro Ser Arg Glu Glu
            350                 355                 360
Met Thr Lys Asn Gln Val Ser Leu Thr Cys Leu Val Lys Gly Phe
            365                 370                 375
Tyr Pro Ser Asp Ile Ala Val Glu Trp Glu Ser Asn Gly Gln Pro
            380                 385                 390
Glu Asn Asn Tyr Lys Thr Thr Pro Pro Val Leu Asp Ser Asp Gly
            395                 400                 405
Ser Phe Phe Leu Tyr Ser Lys Leu Thr Val Asp Lys Ser Arg Trp
            410                 415                 420
Gln Gln Gly Asn Val Phe Ser Cys Ser Val Met His Glu Ala Leu
            425                 430                 435
His Asn His Tyr Thr Gln Lys Ser Leu Ser Leu Ser Pro Gly
            440                 445
```